Figure 1:
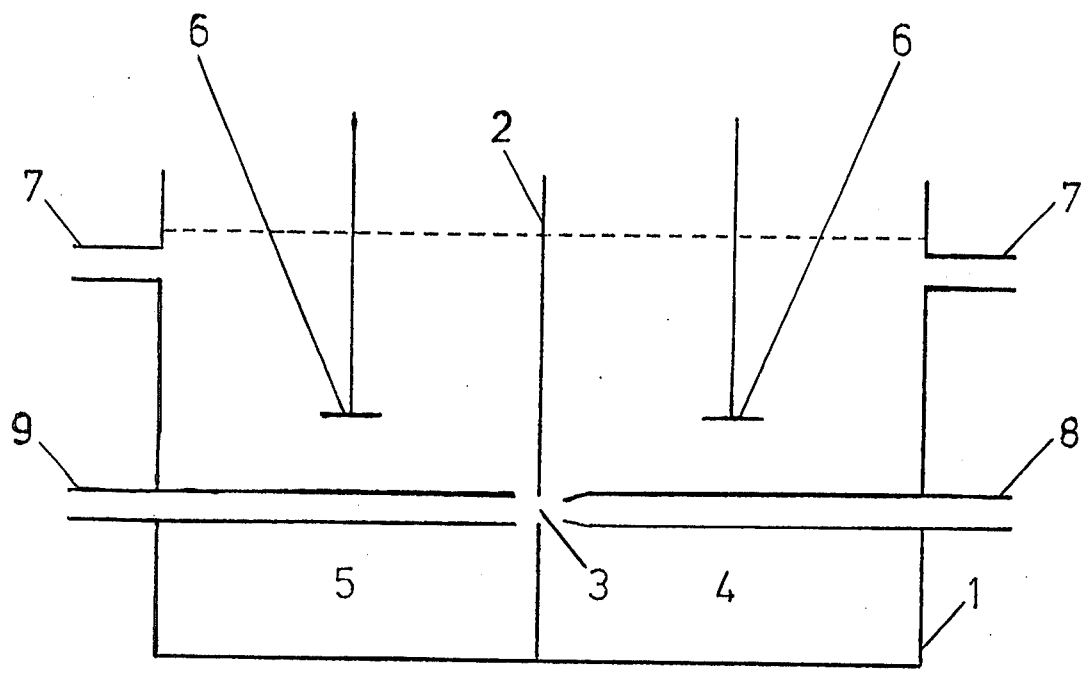

United States Patent [19]

Zimmermann et al.

[11] 4,154,668

[45] May 15, 1979

[54] DEVICE FOR INCREASING THE PERMEABILITY OF THE SKIN OF CELLS OF LIVING BEINGS

[75] Inventors: Ulrich Zimmermann, Jülich; Friedrich Riemann, Bad Salzufler; Gunter Pilwat, Jülich, all of Fed. Rep. of Germany

[73] Assignee: Kernforschungsanlage Jülich Gesellschaft mit beschränkter Haftung, Jülich, Fed. Rep. of Germany

[21] Appl. No.: 750,677

[22] Filed: Dec. 15, 1976

Related U.S. Application Data

[62] Division of Ser. No. 546,771, Feb. 3, 1975, abandoned.

[30] Foreign Application Priority Data

Feb. 2, 1974 [DE] Fed. Rep. of Germany ....... 2405119

[51] Int. Cl.² ............................................. G01N 27/40
[52] U.S. Cl. ............................. 204/299 R; 204/180 R
[58] Field of Search ......................... 204/180 R, 299; 195/1.8

[56] References Cited

U.S. PATENT DOCUMENTS 3,551,554  12/1970  Herschler .................. 195/1.8 X

OTHER PUBLICATIONS

Rose, "The Condensed Chemical Dictionary," 7th Ed., 1966, pp. 243 & 555.

Primary Examiner—Arthur C. Prescott
Attorney, Agent, or Firm—Walter Becker

[57] ABSTRACT

A device for increasing the permeability of the skin of cells of living beings, according to which the respective cells are introduced in the form of a suspension into an electrically conductive liquid thereby there is formed a physiological electrolyte solution which is passed into one of two chambers through a passage of a partition. This partition separates a container into these two chambers, each chamber having an electrode. This passage surrounds the focus of an electric field. The cells in the electrolyte solution are exposed to the electric field while passing from one chamber to the other chamber until macromolecules having a radius of at least 5° are exchanged through the cell skin between the solution in the interior of the cells and the physiological electrolyte solution.

4 Claims, 2 Drawing Figures

DEVICE FOR INCREASING THE PERMEABILITY OF THE SKIN OF CELLS OF LIVING BEINGS

This is a division of an originally copending parent application Ser. No. 546,771—Zimmermann et al filed Feb. 3, 1975 (Monday) now abandoned after being replaced by a copending continuation-in-part application Ser. No. 762,320—Zimmermann et al filed Jan. 25, 1977, now U.S. Pat. No. 4,081,340—Zimmermann et al issued Mar. 28, 1978.

The present invention relates to increasing the permeability of the skin of cells of living beings and means for practicing same. The purpose of increasing the permeability of the skin of cells of living beings consists in introducing into the cells soluble substances which are characterized by desired chemical or physical properties in order to separate said substances from an aqueous solution. This brings about the advantage that catalytically effective substances are absorbed into the interior of the cells.

According to the present invention in a manner not previously known or suggested, cells of living beings are introduced into a solution containing complex formers or catalytically effective substances with an osmolarity lower than that of the cell contents. In view of the increased permeability of the cell skin, there occurs an exchange of the substance between the solution contained in the interior of the cell on one hand and the solution containing the complex formers or catalytically effective substances on the other hand. Thereupon the osmolarity of the solution containing the cells is increased by the addition of osmotically active substances such as calcium ions, sodium ions and potassium ions to the osmolarity of the cell contents of the originally introduced cells in connection with which the cell skin loses it permeability for the complex formers or catalytically effective substances contained in the interior of the cells, thereby enclosing said complex formers or catalytically effective substances. Cells treated in this way and containing complex formers are utilized for ionized substances characterized by chemical or physical properties being separated from an aqueous solution. In this connection, the cells containing the complex formers are introduced into the aqueous solution containing the ionized substances so that the ionized substances pass through the cell skin acting as a diaphragm and are converted by said complex formers into complexes which are difficult to dissociate or difficult to be dissolved. When the cells are separated from the aqueous solution, also the ionized substances bound in said cells are separated from the aqueous solution.

Cells containing catalytically effective substances are utilized for building up or for the decomposition of substances characterized by chemical properties and contained in an aqueous solution. The cells are inserted into the aqueous solution until the substances to be built up or to be decomposed and contained in the aqueous solution have, due to the permeability of the skin of the cells, moved into the interior of the cells. The building up or decomposition of the substances is completed, and the substances have moved through the skin of the cells into the aqueous solution whereupon the built-up or decomposed substances are separated from the aqueous solution in a manner known per se.

The suggested step for bringing about an increase in the permeability, according to which the cells are introduced into a solution with an osmolarity lower than the osmolarity of the cell contents is time-consuming, however. The same is rather time-consuming because the increase in the permeability occurs only slowly. In addition thereto, a plurality of factors important for this method step have to be taken into consideration.

Moreover, if bacterial cells are employed as cells and it is necessary to remove the cell wall, an additional step known per se has to be resorted to in order to separate the cell wall.

It is an object of the present invention to provide a method of increasing the permeability of the skin of cells of living beings, which can be practiced in a simple, quick, and thus economical manner. Thus an increase in the permeability will be realized which makes possible a maximum exchange of macromolecules contained in the interior of the cells and in a solution into which the cells have been introduced. The macromolecules have a radius of at least 5 Å. It is a further object of this invention to provide a method as set forth in the preceding paragraph in which the obtained increase in the permeability will be curable by a simple method.

It is still another object of this invention to provide a device for carrying out the method according to the invention.

These and other objects and advantages of the invention will appear more clearly from the following specification in connection with the accompanying drawings, in which:

FIG. 1 diagrammatically illustrates a section through a device according to the invention which comprises a container divided by a partition into two chambers.

Figure 2:
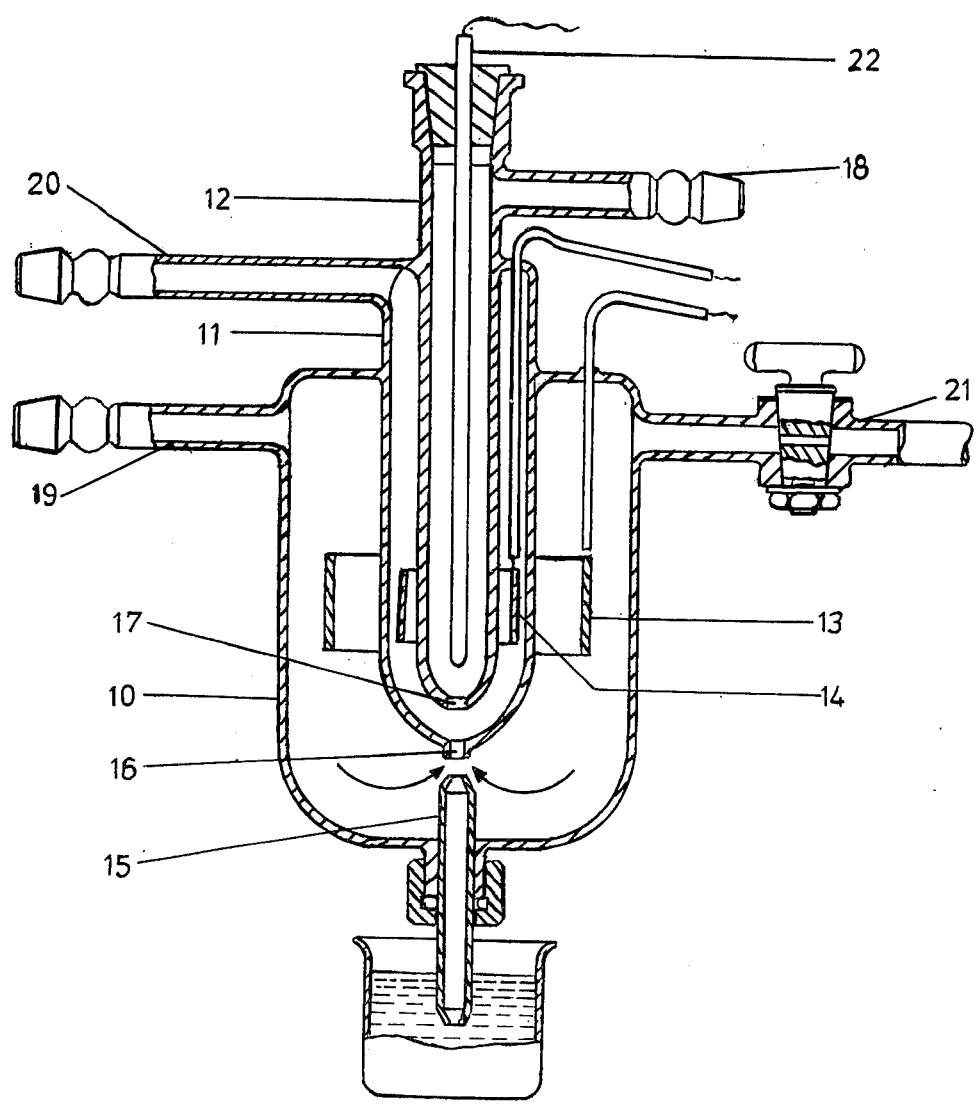

FIG. 2 illustrates a section through a device according to the invention which comprises three coaxially arranged containers.

The present invention for increasing the permeability of the skin of cells of living beings is characterized primarily in the following. The cells are introduced into a liquid forming a suspension and having a temperature of between 0° and 25° C. while being conductive for electric current and forming a physiological electrolyte solution. The thus formed physiological electrolyte solution which contains the cells is exposed to an electrical field until macromolecules having a radius of at least 5 Å are exchanged through the cell skin acting as a diaphragm between the solution contained in the interior of the cell and the physiological electrolyte solution. The field intensity of the field bringing about the increase in permeability, expediently amounts to approximately from $10^3$ to $10^5$ V/cm.

The present invention can be carried out in a discontinuous as well as in a continuous manner. For carrying out the method in a discontinuous manner, a container having two electrodes arranged therein is filled with a physiological electrolyte solution as suspension which contains cells of living beings, and an electric pulse is emitted onto the electrolyte solution.

The present invention when carried out in a continuous manner, occurs in a container filled with a physiological electrolyte solution having a constant electrical field applied to the electrodes of said electrolyte solution. The physiological electrolyte solution containing the cells as suspension is passed through said electrical field. This is advantageously carried out by feeding fresh physiological electrolyte solution containing the cells as suspension in a continuous manner into said container; at the same time the electrolyte solution containing the cells and exposed to the electrical field is withdrawn from the container. At the same time, the heat generated in the electrical field in the electrolyte solution is withdrawn. A highly advantageous method according to the invention consists in that the physiological electrolyte solution which contains the cells as suspension is passed through the focus of a focused electrical field. In this way a better exploitation of the electrical field will be realized, and at the same time it will be assured that the cells which have been carried through the electrical field will all be exposed to an approximately identical field intensity.

The time that the cells stay in the electrical field bringing about the increase in the permeability, as necessary for increasing the permeability of the cell skin, is very short. Thus cells with increased permeability of the cell skin can be prepared in a simple manner and quickly and additionally at a high yield.

An advantageous modification according to the present invention consists in that the physiological electrolyte solution which contains the cells passes through an opening surrounding the focus of the electrical field. This opening is provided in a wall formed of electrically non-conductive material and being arranged between the electrodes of the electrical field. In this way, a still better exploitation of the electrical field will be realized while all cells are exposed to practically the same electrical field. At the same time it will also be brought about that the exchange of macromolecules through the cell skin acting as diaphragm will occur even more completely. This will be recognized for instance when utilizing erythrozytes, by way of the discoloration of the electrolyte liquid in view of hemoglobin exiting from the interior of the cell and by the discoloration of the erythrozytes.

The present invention is advantageously carried out by a device comprising a container divided into two chambers by a partition. A passage in the partition has a diameter of at least 20 $\mu$m. The partition is formed of electrically non-conductive material such as glass or the like. In the chambers there are electrodes respectively arranged one in each chamber. The container wall surrounding said chambers is provided with conduit connection for feeding physiological electrolyte solutions. Into one chamber there extends a feeding nozzle passing through the container wall and directed to said passage. The feeding nozzle is intended for the physiological electrolyte solution containing the cells. Into the other chamber there extends a suction line for the physiological electrolyte containing the cells. The suction line extends through the container wall and is likewise directed toward said passage.

For carrying out the invention, the diameter and the length of the passage and the electrical field applied to the electrodes depending on the desired flow-through are so dimensioned that the desired increase in the permeability of the cell skin will be effected.

An advantageous modification of the device for carrying out the invention consists therein that three containers are provided which are formed of an electrically non-conductive material such as glass or the like. The containers are coaxially arranged with regard to each other so as to form an outer chamber, an intermediate chamber and an inner chamber. The outer chamber is provided with three conduit connections for feeding physiological electrolyte solution and for venting purposes. In the outer container there is provided an electrical passage for the electrodes arranged in the outer chamber. In the center of the bottom of the outer container there is provided a nozzle extending into said outer container for feeding thereinto the physiological electrolyte solution containing the cells. The upper part of the intermediate container is provided with a conduit connection for feeding into said intermediate container a physiological electrolyte solution. The upper portion of the intermediate container is furthermore provided with a passage for passing therethrough the inner electrodes coaxially arranged in the intermediate container with regard to the outer electrodes. The intermediate container at the bottom has a passage located opposite the opening of the feeding nozzle and having a diameter of at least 20 $\mu$m. In the upper portion of the inner container there is provided a conduit connection for withdrawing electrolyte solution containing the cells, and there is furthermore provided a passage for a thermo element. The inner container has its bottom provided with an opening which is located opposite to the opening of the feeding nozzle and opposite to the passage in the bottom of the intermediate container. After the catalytic substances have been received by the interior of the cells, the increase in the permeability of the skin of the cells is curable by heating the solution containing the cells for a period of from 1 to 2 hours to a temperature between 15° and 40° C. In other words, the increased permeability in this way will be restored to its previous permeability. When utilizing bacteria cells, the cells are expediently heated to a temperature of approximately 20° C., and when utilizing erythrozytes, the latter are expediently heated to a temperature of approximately 37° C. Due to the fact that the increased permeability of the cell skin is curable, the cells are usable for receiving macromolecules of various types and thus for various purposes of application.

The cells of living beings made in conformity with the method according to the invention are advantageously also applicable in methods for separating ionized substances. These substances are characterized by chemical or physical properties such as heavy metal ions or the like, separated from a dissolved mixture of substances contained in an aqueous solution. The solution comprises at least 0.5mM magnesium ions and/or calcium ions and potassium ions such as sea water, fresh water, waste water or the like. Such separation may be effected by means of an organic or inorganic complex former aiding such separation and adapted to form a compound with the substances to be separated. The cells are inserted into a solution which contains the complex formers having an osmolarity which differs within limits from the osmolarity of the cell content of the original cells and from the osmolarity of the aqueous solution. This insertion takes place due to an exchange of substances through the cell skin acting as diaphragm. The exchange occurs until a balanced condition is attained between the solution contained in the interior of the cell and the solution containing the complex former. Then the cell content for all practical purposes corresponds to the solution containing the complex former. For purposes of curing the increase in the permeability, the solution containing the cells after being heated for approximately from one to two hours will be held at a temperature within the range of from 15° to 40° C. Subsequently thereto, the cells containing the complex former are separated from the solution containing the complex former. For purposes of enriching the ionized substances contained in the aqueous solution, the cells are inserted into the aqueous solution until the ionized substances to be separated from the aqueous solution have moved through the cell skin acting as diaphragm into the interior of the cells and have been converted by the complex formers into complexes difficult to be dissociated and difficult to dissolve. In a second method step known per se, subsequently the cells are separated from the aqueous solution.

The cells of living beings made in conformity with the method of the invention are also applicable in an advantageous manner to methods for building up and decomposing substances characterized by chemical properties and dissolved in an aqueous solution containing at least 0.5 mM magnesium ions and/or calcium ions and/or potassium ions. This build-up and decomposition may be effected by means of catalytically effective substances aiding said build-up or said decomposition. In this connection, the cells are inserted into a solution containing catalytically effective substances. The osmolarity of this solution deviates in limits from the osmolarity of the cell content of the original cells and from the osmolarity of the aqueous solution. This insertion will continue until due to the increased permeability of the cell skin by the exchange of solution content in the interior of the cell and the solution containing the catalytically effective substances, the cell content corresponds for all practical purposes to the solution containing the catalytically effective substances. Thereupon the solution containing the cells after being heated for approximately one to two hours is held at a temperature within the range of from 15° to 40° C. Thereupon the cells containing the catalytically effective substances are separated from the solution containing the catalytically effective substances. For carrying out the method for building up or decomposing substances, the cells are inserted into the aqueous solution until the substances to be built up or to be decomposed contained in the aqueous solution have moved through the cell skin acting as diaphragm. The substances thus pass into the interior of the cells until the build-up or the decomposition of the substances have moved through the skin of the cells into the aqueous solution. The substances which have been built up or decomposed are separated from the aqueous solution then in a manner known per se.

Referring now to the drawing in detail, the container 1 is divided into two chambers 4 and 5 by means of partition 2 which has a passage 3 therein. In each of said chambers 4 and 5 there is arranged an electrode 6. The container wall is provided with conduit connections 7 for separately passing physiological electrolyte solution into the chambers 4 and 5. For purposes of carrying out the method according to the invention physiological electrolyte solution containing cells is conveyed from the outside to the chamber 4 through a feeding nozzle 8 and through the passage 3 which surrounds the focus of the electrical field and is then withdrawn from container 1 through withdrawal pipe 9 and is collected in a cooled collecting vessel (not shown in FIG. 1) which precedes the suction pump. The loss is physiological electrolyte solution is compensated for by way of the feeding lines 7.

FIG. 2 shows a further developed device according to the invention which comprises three coaxially arranged containers 10, 11 and 12 namely an outer container, an intermediate container and an inner container. In the outer and intermediate containers there are arranged electrodes 13 and 14. For carrying out the method according to the invention, the electrolyte solution containing the cells is conveyed through a jet capillary 15 to the outer chamber and through an orifice 16 provided in the intermediate container 11 and surrounding the electrical field and is further passed through an opening 17 in the inner container 12. This is effected by drawing in electrolyte solution through the connection or nipple 18. The drawn off cells are collected in a cooled collecting vessel not illustrated which precedes the suction pump. The loss in physiological electrolyte solution which occurs when carrying out the method in the device, is equalized through the conduit connections 19 and 20. The conduit connection 21 merely serves for venting the apparatus. In order to exclude any too strong heating and thereby damaging of the cells, a thermo element or thermo couple 22 is provided for controlling the temperature in the inner chamber.

EXAMPLE

Approximately 100 ml of fresh cattle blood was collected in an isotonic sodium citrate solution and the thus formed solution was centrifuged off in a centrifuge at 1200g. Subsequently thereto, approximately 30 ml of the centrifuged off concentrated erythrozytes were washed twice while a corresponding centrifuging was effected. This washing was carried out in a 100 ml of a buffer solution which contained 150 mM NaCl, 16 mM KCl, 4 mM $MgCl_2$, 2 mM $CaCl_2$ and 5 Tris per liter and the pH value of which as adjusted to 7.4 by the addition of hydrochloric acid. Subsequently, the erythrozyte concentrate was diluted with buffer solution to which was added 1 mM adenosin-triphosphate per liter at a ratio of 10:3.

Thereupon the solution containing the erythrozytes was drawn through the jet capillary 15 of a device illustrated in FIG. 2. To this solution there was added at the same time a buffer solution which was cooled to 0° C. and served as physiological electrolyte solution. The diameter and the length of the orifice 16 provided in the intermediate container 11, and the distance of the tip of the feeding jet capillary 15 from the orifice 16 mounted to 0.5 mm. A voltage of 350V was applied to the electrodes. The flow-through of the erythrozytes through the device was so selected that the inserted quantity of the erythrozytes had passed through the device within approximately 30 minutes. The erythrozytes collected in the collecting vessel were centrifuged off for about 15 minutes at a temperature of 0° C. and 13,000 g. From the centrifuged off erythrozytes, subsequently 0.5 ml were suspended in a solution of 5 ml buffer solution and 0.2 ml of an iodine $^{131}$-albumin solution having the specific activity thereof amounting to 0.1 mCi/ml, and held for about an hour at 0° C. Thereupon the erythrozytes were centrifuged off for 15 minutes at 13,000 g, and the centrifuged off erythrozytes were washed twice in a buffer solution while each time a centrifuging off was effected. Said buffer solution contained 0.1% albumin as carrier.

The activity of the iodine$^{131}$-albumin remaining in the erythrozytes after the decomposition of the erythrozytes was measured in a triCarb-liquid scintillator. The measured activity corresponding to a 31% absorption of iodine$^{131}$-albumin by the erythrozytes from the solution containing iodine$^{131}$-albumin.

It is, of course, to be understood that the present invention is, by no means, limited to the specific showing in the drawing and the specific example set forth above, but also comprises any modifications within the scope of the appended claims.

What we claim is:

1. A device in combination according to claim 1, which includes a non-conducting partition separating said first and second chambers and containing said conduit means.

2. A device for increasing the permeability of the skin of cells of living beings which includes in combination: container means comprising an outer chamber, an intermediate chamber and an inner chamber, said three chambers being arranged coaxially with regard to each other and one within the other while having inner surfaces of electrically non-conductive material, said outer container being provided with two connections for respectively introducing into said outer container physiological electrolyte solution and for venting said outer container, first electrode means arranged separately in said outer container, said outer container being provided with a bottom, nozzle means arranged in said bottom for conveying physiological electrolyte solution into said outer container, said intermediate container having an upper section provided with conduit means for introducing into said intermediate container physiological electrolyte solution, second electrode means provided separately in said intermediate container and coaxially arranged with regard to said first electrode means, said intermediate container having a bottom with an opening arranged in approximately axial alignment with said nozzle means and located opposite thereto and having a diameter of at least 20 μm, said inner container having an upper portion provided with a conduit connection for withdrawing electrolyte solution containing cells directly from said inner container, said inner container also comprising passage means, and a thermo coupled passing through said last mentioned passage means, said inner container having a bottom provided with an opening therethrough arranged in approximately axial alignment with the opening in the bottom of said intermediate container and located opposite said last mentioned opening.

3. A device in combination according to claim 1, which includes a partition non-conducting separating said first and second chambers and containing said conduit means.

4. A device for increasing the permeability of the skin of cells of living beings which includes in combination: container means comprising an outer chamber, an intermediate chamber and an inner chamber, said three chambers being arranged coaxially with regard to each other and one within the other while having inner surfaces of electrically non-conductive material, said outer container being provided with two connections for respectively introducing into said outer container physiological electrolyte solution and for venting said outer container, first electrode eans arranged separately in said outer container, said outer container being provided with a bottom, nozzle means arranged in said bottom for conveying physiological electrolyte solution into said outer container, said intermediate container having an upper section provided with conduit means for introducing into said intermediate container physiological electrolyte solution, second electrode means provided separately in said intermediate container and coaxially arranged with regard to said first electrode means, said intermediate container having a bottom with an opening arranged in approximately axial alignment with said nozzle means and located opposite thereto and having a diameter of at least 20 μm, said inner container having an upper portion provided with a conduit connection for withdrawing electrolyte solution containing cells directly from said inner container, said inner container also comprising passage means, and a thermo couple passing through said last mentioned passage means, said inner container having a bottom provided with an opening therethrough arranged in approximately axial alignment with the opening in the bottom of said intermediate container and located opposite said last mentioned opening.

* * * * *